(12) United States Patent
Tjandrawinata et al.

(10) Patent No.: US 9,078,917 B2
(45) Date of Patent: Jul. 14, 2015

(54) **EXTRACT OF *PHALERIA MACROCARPA* AS AN ANTINEOPLASTIC, ANTI-INFLAMMATORY AND ANTIANGIOGENIC AGENT**

(75) Inventors: Raymond R. Tjandrawinata, Tangerang (ID); Asep Aripin, Tangerang (ID); Poppy Firzani Arifin, Tangerang (ID); Dina Rahmi, Tangerang (ID)

(73) Assignee: PT. Dexa Medica, Palembang (ID)

( * ) Notice: Subject to any disclaimer, the term of this patent is extended or adjusted under 35 U.S.C. 154(b) by 341 days.

(21) Appl. No.: 12/997,171

(22) PCT Filed: Jun. 8, 2009

(86) PCT No.: PCT/IB2009/052407
§ 371 (c)(1),
(2), (4) Date: Dec. 9, 2010

(87) PCT Pub. No.: WO2009/153692
PCT Pub. Date: Dec. 23, 2009

(65) Prior Publication Data
US 2011/0091395 A1    Apr. 21, 2011

(30) Foreign Application Priority Data
Jun. 16, 2008 (ID) .............................. P00200800334

(51) Int. Cl.
*A61K 36/00* (2006.01)
*A61K 36/83* (2006.01)

(52) U.S. Cl.
CPC ...................................... *A61K 36/83* (2013.01)

(58) Field of Classification Search
None
See application file for complete search history.

(56) References Cited

U.S. PATENT DOCUMENTS

2007/0248694 A1* 10/2007 Subbiah .................. 424/725

OTHER PUBLICATIONS

Sugiwati et al, alpha.-glucosidase inhibitory activity and hypoglycemic effect of *Phaleria macrocarpa* fruit pericarp extracts by oral administration to rats, Journal of Applied Sciences (2006), 6(10), 2312-2316.*
Faried et al, Anticancer effects of gallic acid isolated from Indonesian herbal medicine, *Phaleria macrocarpa* (Scheff.) Boerl, on human cancer cell lines. International journal of oncology, (Mar. 2007) vol. 30, No. 3, pp. 605-613.*
Liu et al, Gallic acid is partially responsible for the antiangiogenic activities of *Rubus* leaf extract. Phytotherapy research : PTR, (Sep. 2006) vol. 20, No. 9, pp. 806-813.*
Indonesian Patent Application P00 2005 00077 A (KANTOR HKI-IPB) Aug. 16, 2006 (cited in application).
Fared, A. et al., Anticancer Effects . . . International Journal of Oncology. 2007, vol .30, No. 3, pp. 605-613.
Oshimi, S. et al., Studies . . . Journal of Natural Medicines. Apr. 2008, vol. 62, No. 2, pp. 207-210.
Kurnia, D. et al., "29-Norcucurbitacin . . . " Bioscience, Biotechnology and Biochemistry. Feb. 2008, vol. 72, No. 2 pp. 618-620.
ISR attached to WO/2009/153692.
PCT/IPEA/408 (Written Opinion) in PCT/IB2009/052407.
Arguments to the Written Opinion in PCT/IB2009/052407.
WO/2009/153692 (Application as published by WIPO).

* cited by examiner

*Primary Examiner* — Qiuwen Mi
(74) *Attorney, Agent, or Firm* — Neifeld IP Law, PC

(57) ABSTRACT

A pharmaceutical dosage form comprising an extract of *Phaleria macrocarpa* which has antineoplastic, anti-inflammatory, and antiangiogenic activity. Its use as an antineoplastic agent is to inhibit tumour growth. Its use as an anti-inflammatory agent is to relieve inflammation and pain, and also as an antipyretic. Another use is as an antiangiogenic agent to inhibit the growth of new blood vessels to prevent cancer metastasis.

12 Claims, 6 Drawing Sheets

EXTRACT OF *PHALERIA MACROCARPA* AS AN ANTINEOPLASTIC, ANTI-INFLAMMATORY AND ANTIANGIOGENIC AGENT

FIELD OF THE INVENTION

The present invention relates to a herbal extract of the plant of *Phaleria macrocarpa*, and include the extraction method and description of the biological activities of such extract which include antineoplasia, anti-inflammation, and antiangiogenesis.

BACKGROUND OF THE INVENTION

Neoplasia is an abnormal proliferation of cells within a tissue or an organ, resulting in a structure known as a neoplasm. Tumor is a neoplasm that has formed a lump; while neoplasm may not form a lump, for example cervical intraepithelial neoplasia, anal intraepithelial neoplasia, and leukemia. Neoplasm may be benign, however it can also be malignant. A benign neoplasm includes, for example, leiomyoma or uterine fibroids and melanocytic nevi or moles. A malignant neoplasm includes, for example, teratoma, also various kinds of cancer, including breast cancer.

Breast cancer is the second most occurring cancer in Indonesian women after cervical cancer. Men could also suffer from breast cancer even though the chance is less than that of women. Breast cancer treatment that is commonly used is a surgical removal of the cancer tissue, followed by, if necessary, a chemotherapy or radiation treatment.

Inflammation is a form of a nonspecific response of immune system to a damaged cell. Inflammation is usually characterized by redness, pain, warmth and swelling. There are a number of components which could cause inflammation, however, the component which is closely related to inflammation is prostaglandin, especially the prostaglandin $E_2$ (commonly abbreviated as $PGE_2$). The concentration of $PGE_2$ could be suppressed by nonsteroidal anti-inflammatory drugs (NSAIDs). NSAIDs work by inhibiting cyclooxygenase enzyme, abbreviated as COX, which is an enzyme acting in the formation of prostanoids, including prostaglandins, prostacyclins, and thromboxanes. COX has two isoforms, named COX-1 and COX-2.

COX-1 is a constitutive enzyme, its concentration is stable within a body, it can be found in a majority of tissues, it converts arachidonic acid (AA) to prostaglandin. The prostaglandin then stimulates normal body functions such as secreting mucus in intestine. Normally, COX-2 is undetectable in normal cells, however its expression is inducible. COX-2 plays an important role in inflammation, because its involvement in producing prostaglandin for the inflammatory response. In cells, AA is also important for prostaglandin synthesis. AA from a phospholipid membrane is released into a cell by the enzyme phospholipase $A_2$ ($PLA_2$).

Angiogenesis is a physiological process involving the formation and growth of new blood vessels from pre-existing vessels. Angiogenesis process is a normal process in growth and development, however, it is also a fundamental step in the transition of tumors from a dormant state to a malignant state. Angiogenesis is stimulated by several chemical compounds, one of which is the vascular endothelial growth factor (VEGF). VEGF has a major contribution to angiogenesis by increasing the number of capillaries. VEGF comprises of VEGF-A, VEGF-B, VEGF-C, VEGF-D, and PlGF (Placenta Growth Factor). Recently it was discovered that VEGF-E and VEGF-F are also coded by virus. Based on some literatures, there is a positive correlation at mRNA level between COX-2 and VEGF-C in the tissues and cells of breast cancer.

The fruits and leaves of *Phaleria macrocarpa* plant, also known as Mahkota Dewa, have been used by Indonesian people to overcome various symptoms and diseases, to include treatment of cancer. The Indonesian Patent Application No. P00 2005 00077 taught that the flavonoid of water-processed extract of Mahkota Dewa (*Phaleria macrocarpa*) has the characteristics of an anticancer, based on its ability to reduce the tyrosine kinase activities, its antioxidant activities, and its activities against HeLa cancer cells proliferation.

Within the current invention, the data will be described showing the effects of *Phaleria macrocarpa* extract as antineoplastic agent in inhibiting cell growth and its ability to induce breast cancer cell death via the mechanism of apoptosis. In addition, the effects of *Phaleria macrocarpa* extract as anti-inflammatory and antiangiogenic agent will also be described.

BRIEF DESCRIPTION OF THE INVENTION

The objects and/or solutions which are taught from the present invention will be set forth in the preferred embodiments. The embodiments illustrated serve the purpose of understanding the present invention, without limiting the possibilities of other embodiments which can be learned from the practice of the present invention. The objects and/or solutions which are taught in the present invention will be realized from the elements and combinations detailed in the claims herein.

To attain the solutions and in accordance with the objects of the present invention, as explained in the embodiments and broadly described in this application, the first aspect of the present invention is directed to a process of extraction of active ingredients from *Phaleria macrocarpa* fruits, comprising the steps to be described in the Detailed Description of the Invention.

The second aspect of the present invention is directed to an extract or fraction(s) derived from *Phaleria macrocarpa* ripe fruits prepared by said process using organic solvents and water at various ratios, characterized in that the extract or fraction(s) has IC50 less than 50 µg/ml when analyzed on MDA-MB-231 cancer cells in MTT test.

The third aspect of the present invention is directed to a pharmaceutical composition or dietary supplement which comprises the extract of *Phaleria macrocarpa* or its fraction(s) or compound(s) or flavonoid(s) which are derived therefrom, as a single active ingredient or in combination, in the amount or effective dosage to prevent, treat, or provide therapeutic effect against cancer. The pharmaceutical composition or preparation according to this invention also comprises the excipient ingredient which is pharmaceutically acceptable.

The fourth aspect of the present invention is directed to a pharmaceutical composition or preparation which comprises the extract of *Phaleria macrocarpa* which functions as antineoplastic agent against breast cancer as well as other gynecologic pathologic conditions.

The fifth aspect of the present invention is directed to a pharmaceutical composition or preparation which comprises the extract of *Phaleria macrocarpa* which functions as anti-inflammatory agent.

The sixth aspect of the present invention is directed to a pharmaceutical composition or preparation which comprises the extract of *Phaleria macrocarpa* which functions as antiangiogenic agent.

The further aspect of the present invention is directed to the use of the extract of *Phaleria macrocarpa* of the invention for preparing a medicament for treating or preventing various kind of diseases or disorders as described in the Description and Claims.

BRIEF DESCRIPTION OF THE DRAWINGS

The accompanying drawings, which are incorporated in and constitute a part of the specification of the present application, illustrate one or several embodiments of the invention. These drawings serve to explain the principles which are taught by the present invention.

DETAILED DESCRIPTION OF THE INVENTION

Figure 1:
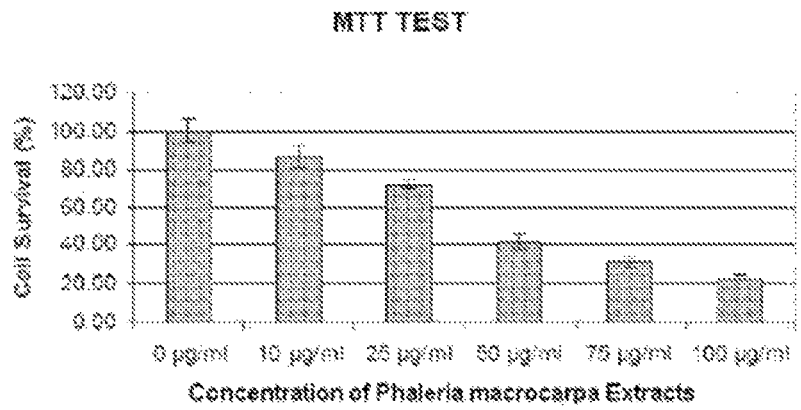
FIG. 1 shows the effect of the *Phaleria macrocarpa* extract to the proliferation of MDA-MB-231 cancer cells.

Reference will now be made in detail by ways of examples without limiting the scope of the invention to the examples provided.

The *Phaleria macrocarpa* extract according to the teaching of the present invention originally comes from the fruits of *Phaleria macrocarpa*. The fruits being used are ripe fruits of *Phaleria macrocarpa*. The plants *Phaleria macrocarpa* grow in various location inside and outside of Indonesia. It is preferred that the *Phaleria macrocarpa* be those planted in the area called Salatiga, Central Java island. It will be described herewith the extraction procedure of *Phaleria macrocarpa*.

A. Extraction Process of *Phaleria macrocarpa* (Scheff.) Boerl

Raw material: Ripe fruits of *Phaleria macrocarpa* cut in half, then diced.

Solvent: The solvent used for the extraction is an organic solvent, such as ethyl acetate, alcohol including methanol, ethanol, n-butanol either absolute or mixed with water in various ratios. Sodium sulphate anhydrate GR is used to withdraw water from its organic fraction. For the purpose of Thin Layer Chromatograph (TLC) analysis, silica gel aluminum plate, chloroform GR, and methanol GR are used. In order to visualize TLC spots, an acid solution may be used. Cotton is also needed for the filtration process.

Instruments: Some of the equipments used include a rotary vacuum evaporator (rotavapor), a heat-gun and a disk-mill. An ultra-violet lamp is also needed. Other apparatus includes an erlenmeyer flask, a funnel, a separating funnel, an evaporator flask, measuring glass, and a spatula.

Extraction process: The flesh of *Phaleria macrocarpa* fruits is grounded using a disk-mill machine until dry powder is obtained. The dry powder is extracted using an organic solvent. The extraction process is performed in several stages. The filtrate resulted from the various stages of extraction is mixed and then dried to evaporate the solvent using the rotavapor in a vacuum condition until the desired extract is obtained.

To obtain the active extract of *Phaleria macrocarpa*, the resulting extract from the above process is fractionated by liquid-liquid extraction in a separating funnel using an organic solvent and water, and then agitated until two fully distinguished phases are formed, the organic phase is separated. To optimize the resulting organic phase, a liquid-liquid extraction process is performed. The resulting organic phase is combined with and added to anhydrous salt to withdraw the water molecules. The organic phase is then dried to evaporate the solvent using a rotavapor in a vacuum condition thus the *Phaleria macrocarpa* extract is obtained. Using this method, the resulting *Phaleria macrocarpa* extract has a semi-solid form with a distinguished smell and has a yellowish-brown color. The *Phaleria macrocarpa* extract is then characterized with a TLC and the results are stored; such data will be used as a comparison for subsequent processes.

The resulting extraction of *Phaleria macrocarpa* fruits in accordance with the teaching of the present invention contains at least the compound of alkaloid, terpenoid, saponin, resin, flavonoid, and polyphenol, as well as other secondary metabolites or their combinations which can deliver specific biological effects.

B. Antineoplastic Effects of *Phaleria macrocarpa* Extract in MDA-MB-231 Cancer Cells In testing *Phaleria macrocarpa* extract as antineoplastic agent, will be taught herein also about the effects of *Phaleria macrocarpa* extract as anti-proliferation and apoptosis effects of *Phaleria macrocarpa* extract in MDA-MB-231 cancer cells.

Methods

MDA-MB-231 cells were cultured in supplemented medium, then the cells were incubated at 37° C., 5% $CO_2$.

Anti-Proliferation Assay of MDA-MB-231 Cancer Cells

This assay was performed using 96-well plates. Each well contains certain cell density. After 24 hours incubation, medium was changed with serum-free medium, then the cell culture was added with *Phaleria macrocarpa* extract sample in various concentrations. The cells were then incubated; the alive cells after treatment were, determined using cell death determination assay, MTT assay. The absorbance value was read in microplate reader. After converted with standard curve, from the absorbance value, then the numbers of alive and death cells were obtained.

The percentage of the number of alive cells in every treatment was determined by counting the number of alive cells in wells received the extract treatments divided the number of alive cells in control cells then multiplied with 100%.

% Number of alive cells=$B/A \times 100\%$ where, A is the number of alive cells in control cells, and B is the number of alive treated-cells. IC50 value is a number showing concentration of a sample that causes cell death as much as 50% of the cell population. The value was obtained by using ProStat statistical program.

DNA Fragmentation Analysis

Apoptosis is an active process of cell death that is characterized by chromosome DNA cleavage, chromatin condensation, and DNA fragmentation. In this experiment, the effect of *Phaleria macrocarpa* extract administration was observed toward the formation of DNA fragmentation, one of characteristics of apoptosis. MDA-MB-231 cells were cultured in plates. After 24 hours incubation, *Phaleria macrocarpa* extract was added in various concentrations. Determination of DNA fragmentation was performed using DNA Apoptosis Ladder Kit. DNA fragmentation was observed on electrophoresis gel visualized using ethidium bromide.

RNA Isolation and Reverse-Transcription PCR (RT-PCR)

$BCl_2$ and Bax are genes that are active in apoptosis process. To identify the mRNA expression of $BCl_2$ and Bax, RT-PCR was performed. RNA total was first isolated from MDA-MB-231 cells. RNA isolation products were quantified using spectrophotometer and visualized by electrophoresis technique on agarose gel. The RNAs were then used in RT-PCR process using specific primers. RT-PCR process was performed in a PCR machine in an optimized condition.

Caspase 9 Activity Assay

One of the indicators that apoptosis is occurring is the increase of caspase 9 enzyme activity. In this experiment, Caspase 9 Assay Kit Colorimetric was used. This assay based on spectrophotometer detection of chromophore p-nitroanilide (pNA). pNA light emission can be quantified by using spectrophotometer. The ratio of absorbance value from pNA treated-sample was compared to control. This assay was done according to manufacturer's protocol.

Animal Study

To ensure the effects of *Phaleria macrocarpa* extract treatments to the tumor formation, an in vivo study in Balb/C mice was performed. The mice were subcutaneus injected with MDA-MB-231 at 2 nipples for each mouse, where at one nipple induced by a phorbol ester, TPA, with aseptic technique. The extracts were administered to the mice for 12 weeks.

In breast cancer, Cycloxygenase-2 (COX-2) expression was correlated with tumor growth thus it is used as biological marker for breast cancer, while Vascular Growth Endothelial Factor (VEGF) is used as a marker for angiogenesis in metastasis process. To identify the mRNA expression of mRNA COX-2, VEGF-C and $cPLA_2$, RT-PCR was performed following the RNA isolation.

Results

Effects of *Phaleria Macrocarpa* Extracts to the Proliferation of MDA-MB-231 Cancer Cells From the MTT Test results, we obtained a result that *Phaleria macrocarpa* extract showed an anticancer effect in MDA-MB-231 cells. It was shown that significant decrease of cell number percentage occurred as the extract concentrations increased. This was shown in FIG. 1. Percentage alive cells were then used to calculate IC50 value in MDA-MB-231 cells. Referring to the bar chart illustrated in FIG. 1, the IC50 or 50% of Cell Survival can be obtained using the *Phaleria macrocarpa* extract having a concentration of less than 50 μg/ml. According to the ProStat statistical program, the IC50 value obtained for MDA-MB-231 cells was 40.76 μg/ml.

DNA Fragmentation Analysis

Figure 2:
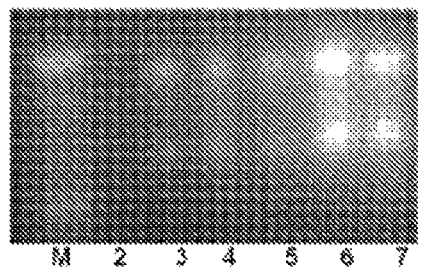
FIG. 2 shows the effect of the *Phaleria macrocarpa* extract to the formation of DNA fragments in MDA-MB-231 cells, notes:
  Col. M: DNA marker;
  Col. 2: Control;
  Col. 3: *Phaleria macrocarpa* extract 25 µg/ml;
  Col. 4: *Phaleria macrocarpa* extract 50 µg/ml;
  Col. 5: *Phaleria macrocarpa* extract 75 µg/ml;
  Col. 6: *Phaleria macrocarpa* extract 100 µg/ml;
  Col. 7: Doxorubicin 10 µg/ml.

Analysis of DNA fragmentation showed that there are DNA fragments in DNA sample obtained from MDA-MB-231 cells. They were treated by *Phaleria macrocarpa* extract at dose 50 μg/ml and 75 μg/ml (FIG. 2).

RNA Isolation and RT-PCR of $BCl_2$ dan Bax

Figure 3:
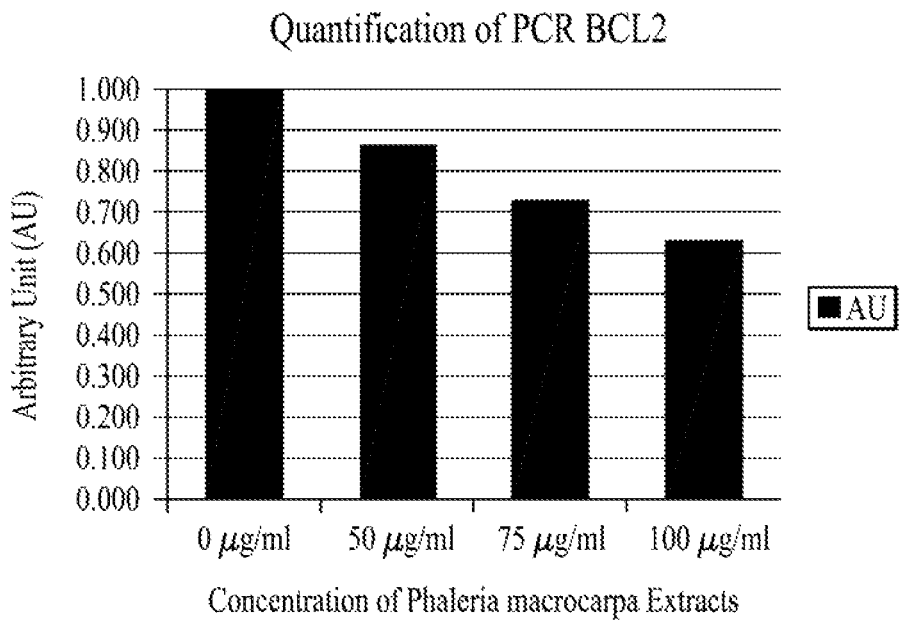
FIG. 3 shows $BCl_2$ RT-PCR results in MDA-MB-231 cells.

From the RT-PCR results using $BCl_2$ primer, down-regulation of $BCl_2$ mRNA expression in MDA-MB-231 cells was found after *Phaleria macrocarpa* extract administration. On the gel, it was shown that amplification bands of $BCl_2$ gene were narrower as the extract concentrations administered were increased. Quantitatively, down-regulation of $BCl_2$ in mRNA level was shown to occur (FIG. 3).

Figure 4:
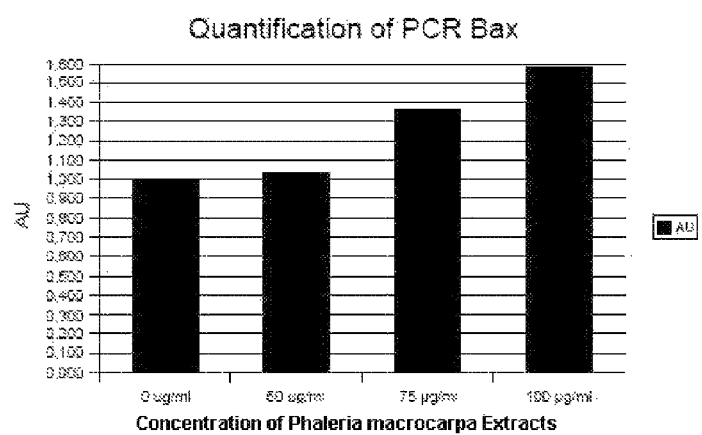
FIG. 4 shows Bax RT-PCR results in MDA-MB-231 cells.

Contrary to that of $BCl_2$, Bax mRNA expression in MDA-MB-231 cells was shown to be upregulated. The data showed that the higher concentration of *Phaleria macrocarpa* extracts, the denser the bands produced (FIG. 4).

Caspase 9 Assay

Figure 5:
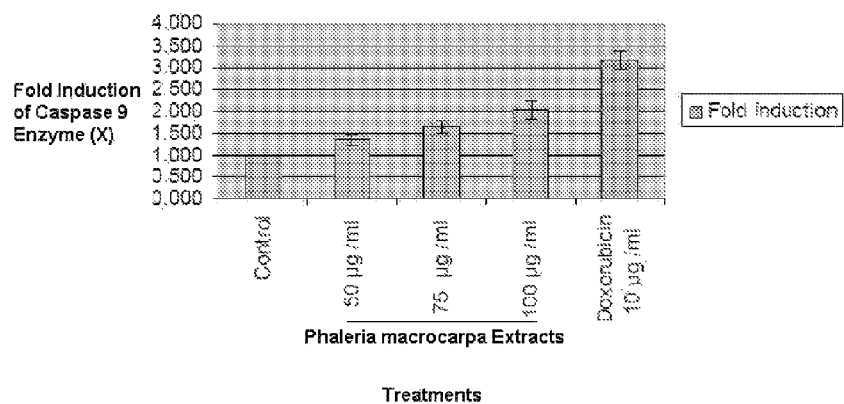
FIG. 5 shows the effect of *Phaleria macrocarpa* extract treatment toward the increase of caspase 9 activities in MDA-MB-231 cells.

Administration of *Phaleria macrocarpa* extract in MDA-MB-231 cells caused significant elevation of caspase 9 activities (FIG. 5).

Animal Study

Figure 6:
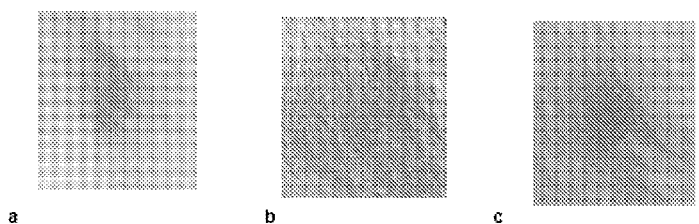
FIG. 6 are pictures of the breast nipples of several MDA-MB-231-injected mice, notes:
  (a) control (without any treatments);
  (b) the nipple of MDA-MB-231-injected and TPA-induced mice;
  (c) the nipple of MDA-MB-231-injected mice.

Injection of tumor cells to mice did not show any tumor lump as expected. Nipples of mice injected with cancer cells and induced with TPA showed redness, however nipples of mice injected with cancer cells showed red spot but not too wide (FIGS. 6a, 6b, and 6c).

Figure 7:
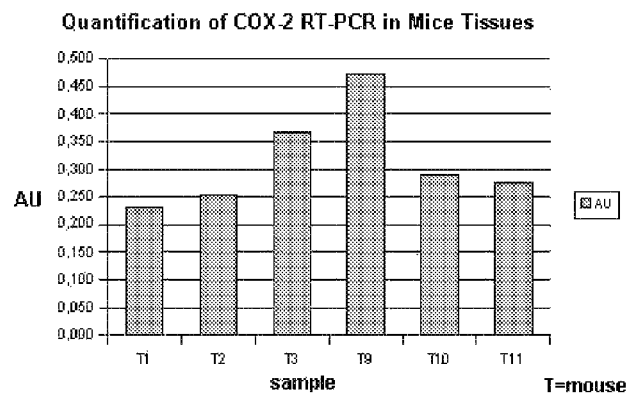
FIG. 7 shows COX-2 RT-PCR results from tissues of mice, notes:
  T1, T2, and T3 are COX-2 mRNA expressions of MDA-MB-231-injected and TPA-induced mice without *Phaleria macrocarpa* extract administration;
  T9, T10, and T11 are COX-2 mRNA expressions of MDA-MB-231-injected and TPA-induced mice with *Phaleria macrocarpa* extract administration.
Figure 8:
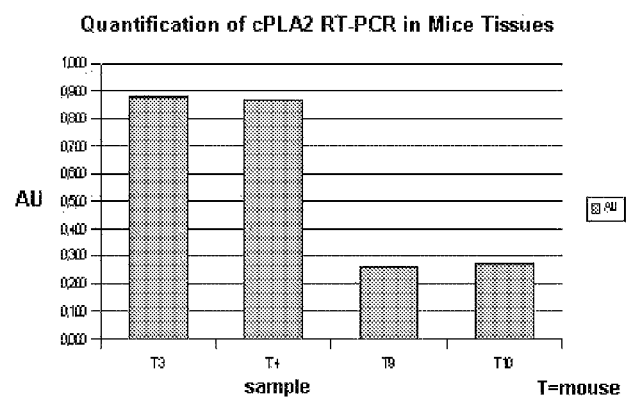
FIG. 8 shows $cPLA_2$ RT-PCR results from tissues of mice, notes:
  T3 and T4 are $cPLA_2$ mRNA expressions of MDA-MB-231-injected and TPA-induced mice without *Phaleria macrocarpa* extract administration;
  T9 and T10 are $cPLA_2$ mRNA expressions of MDA-MB-231-injected and TPA-induced mice with *Phaleria macrocarpa* extract administration.
Figure 9:
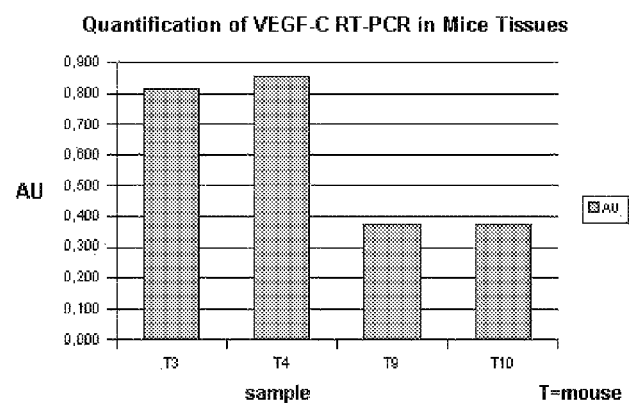
FIG. 9 shows VEGF-C RT-PCR results from tissues of mice, notes:
  T3 and T4 are VEGF-C mRNA expressions of MDA-MB-231-injected and TPA-induced mice without *Phaleria macrocarpa* extract administration;
  T9 and T10 are VEGF-C mRNA expressions of MDA-MB-231-injected and TPA-induced mice with *Phaleria macrocarpa* extract administration.

From the RT-PCR results, COX-2 bands are not always present in the tissues that had not received *Phaleria macrocarpa* extract and there was no COX-2 gene bands in the tissues received *Phaleria macrocarpa* extract (FIG. 7). While in RT-PCR results using VEGF-C and cPLA$_2$ primers, there were a decrease of gene expression level of such genes administered, *Phaleria macrocarpa* extracts. It was shown on the gel that VEGF-C and cPLA$_2$ gene bands were narrower at the sample treated by *Phaleria macrocarpa* extract (FIG. 8, FIG. 9).

Discussion

The MTT assay results showed that *Phaleria macrocarpa* extract was able to inhibit the proliferation of breast cancer cells. In MDA-MB-231 cells, we obtained an IC50 value of less than 50 µg/ml. According to a literature, a substance is called active if it has IC50 value <100 µg/ml. From the above result, it was shown that *Phaleria macrocarpa* extract has the activity as anti-proliferation of breast cancer cells.

After the administration of *Phaleria macrocarpa* extract in MDA-MB-231 cells, the presence of DNA fragments started to appear at dose starting from 25 µg/ml. This was in line with the finding using the MTT.

The RT-PCR results showed a down-regulation of mRNA expression of BCl$_2$ and an up-regulation of mRNA expression of Bax in MDA-MB-231 cells after *Phaleria macrocarpa* extract administration (FIGS. 3 and 4).

BCl$_2$ gene is an oncogene of BCL-2 family member which has an antiapoptotic property. BCL-2 family member is divided into two groups, proapoptosis and antiapoptosis. Cell sensitivity in stimulating apoptosis depends on the balance between proapoptotic and antiapoptotic proteins. If the proapoptotic proteins are abundant, then a cell will tend to undergo apoptosis, but if antiapoptotic proteins are abundant then a cell will tend to resist against death.

In MDA-MB-231 cells, *Phaleria macrocarpa* extract administration caused an increase of caspase 9 which is one of indicators to determine apoptosis. It meant that there was a correlation with another apoptosis indicator, such as up-regulation of Bax gene expression. Bax gene creates a tunnel in mitochondrial membrane and causes the release of cytocrome c, thus helps activating caspase 9 proteolytic enzyme that causes cell to undergo apoptosis.

In animal study, it was shown that cancer cell injection into mice did not produce a tumor/lump as was expected. This might happen due to the limited amount of cancer cells injected and perhaps the cancer cells were not exactly injected into mammary glands, but into tissues nearby. Another possibility was because of the mice we used were not the "nude mice" or "immunosuppressed mice" so the mice we used responded a rejection so they did not develop tumors.

From RT-PCR results using specific primer for VEGF-C, it was shown that there was a decrease in mRNA expression of VEGF-C after *Phaleria macrocarpa* extract administration. It was shown on the gel that bands of amplification products of VEGF-C gene were narrower in the sample that was treated with *Phaleria macrocarpa* extract. It showed that *Phaleria macrocarpa* extract may have antiangiogenic effect. Angiogenesis process is important in tumor growth. The increase of vascular supplies nutrition and oxygen causes the increase of tumor mass.

From RT-PCR results using specific primer for cPLA$_2$, it was shown a decrease of mRNA expression of cPLA$_2$ after *Phaleria macrocarpa* extract administration. It was shown on the gel that bands of cPLA$_2$ gene were narrower in the sample that was treated with *Phaleria macrocarpa* extract. It showed that *Phaleria macrocarpa* extract may have anti-inflammatory effect. From RT-PCR results performed, RT-PCR product of COX-2 in mice tissues were not stable, as evidenced by the bands of COX-2 that were not consistently present. This may have been due to the quality of mice RNAs that were different and unstable.

Conclusion

From the experiments we performed, it could be concluded that *Phaleria macrocarpa* extract inhibits proliferation of breast cancer cells, MDA-MB-231. In MDA-MB-231, IC50 value was 40.76 µg/ml. Indication of apoptosis was shown in MDA-MB-231 cells by DNA fragments, down-regulation of mRNA expression of BCl$_2$, up-regulation of mRNA expression of Bax, and elevation of caspase 9 activities. This conclusion supported the deduction that *Phaleria macrocarpa* extract can be used as an antitumor, curative agent for cervical intraepithelial neoplasia, anal intraepithelial neoplasia, leukemia, or other diseases caused by neoplasia, including leiomyoma also gynecologic pathologic conditions in women.

C. Anti-Inflammatory and Antiangiogenic Effects of *Phaleria macrocarpa* in MDA-MB-231 Cancer Cells The following describe experiment results about *Phaleria macrocarpa* extract as taught in this invention, mainly anti-inflammatory and antiangiogenic effects in MDA-MB-231 cells.

Methods

RNA Isolation and RT-PCR

MDA-MB-231 cells were cultured in supplemented medium, then the cells were incubated at 37° C., CO$_2$ 5%. MDA-MB-231 cells were cultured in 6-well plates. A day before treatment administration, medium was changed with serum-free medium for 24 hours. Treatment administration was done by administering various doses of *Phaleria macrocarpa* extract dissolved in organic solvent. RNA isolation was conducted using Trizol. The RNAs then were used in RT-PCR process using specific primer for each gene we used. RT-PCR reactions were performed in PCR machines with optimized conditions. RT-PCR products were analyzed using electrophoresis technique on agarose gel 2%, and quantified using Chemidoc.

Results

The results showed that there was an inhibition effect of *Phaleria macrocarpa* extract to the expression of COX-2, COX-1, cPLA$_2$, and VEGF-C at mRNA level in serum-free condition in MDA-MB-231 cells.

Figure 10A:
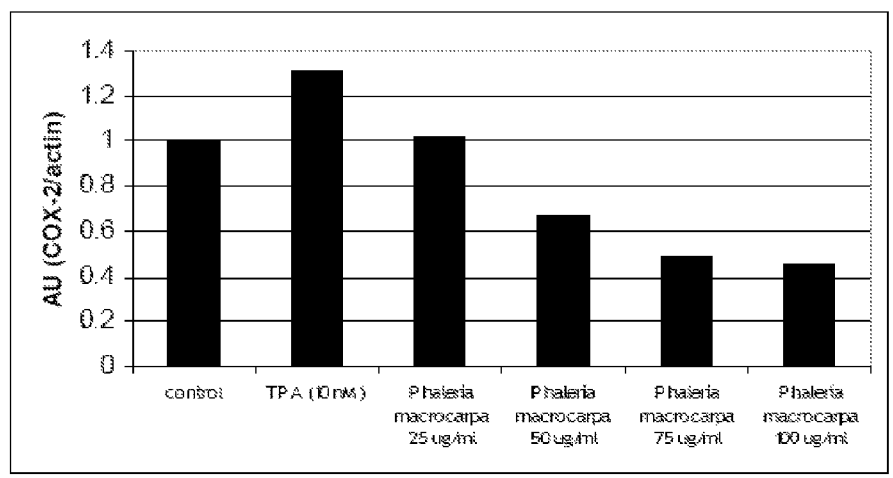
FIG. 10 shows COX-2 RT-PCR results, notes:
  (a) dosage variation of *Phaleria macrocarpa* extract (25-100 µg/ml) in MDA-MB-231 cells for 18 hours; the cells were previously serum-starved for 27 hours;
  (b) dosage variation of *Phaleria macrocarpa* extract (25-100 µg/ml) in MDA-MB-231 cells for 18 hours; the cells were previously serum-starved for 24 hours; induced with TPA 1 hour following the extract administration;
  (c) dosage variation of *Phaleria macrocarpa* extract (25-100 µg/ml) in MDA-MB-231 cells for 18 hours; the cells were previously serum-starved for 24 hours; induced with TPA 1 hour prior to *Phaleria macrocarpa* extract administration.
Figure 10B:
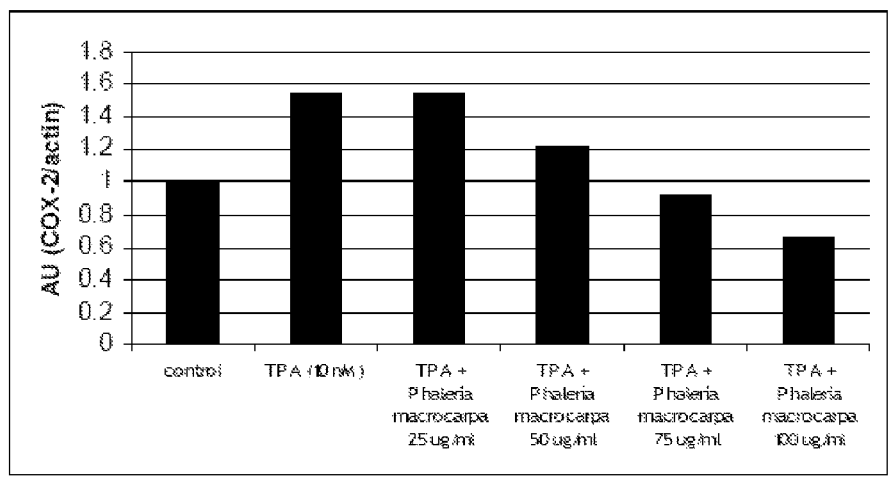
Figure 10C:
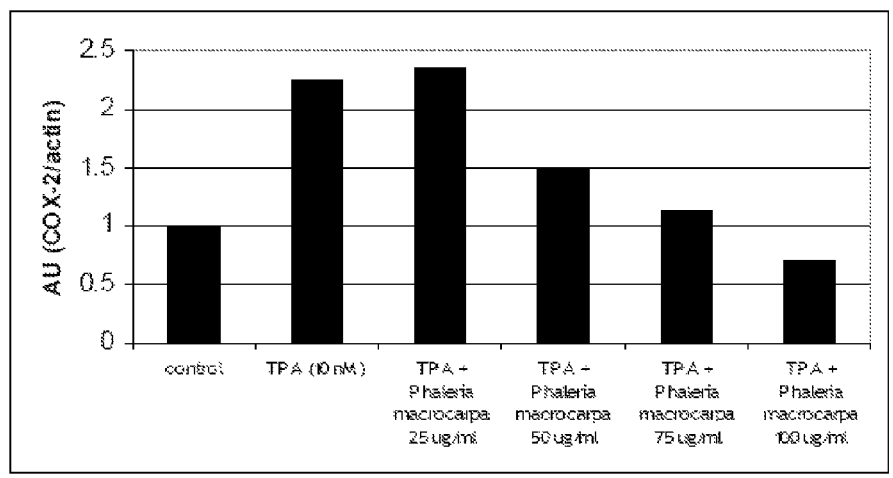

Administration of *Phaleria macrocarpa* extract showed a down-regulation of COX-2 mRNA during 18 hours in MDA-MB-231 cells in serum-free medium by increasing the extract doses. It was shown in the administration of *Phaleria macrocarpa* extract at dose 25-100 µg/ml (FIG. 10a), administration of *Phaleria macrocarpa* extract an hour prior to tumor promoter/TPA induction (FIG. 10b), and administration of *Phaleria macrocarpa* extract an hour following the TPA induction (FIG. 10c). Administration of *Phaleria macrocarpa* extract alone at various dose between 50-100 µg/ml, showed a significant down-regulation of COX-2 compared to control. Administration of 75-100 µg/ml *Phaleria macrocarpa* extract an hour prior to TPA induction, showed a down-regulation of COX-2. Administration of *Phaleria macrocarpa* extract an hour following the TPA induction, showed a significant down-regulation of COX-2 compared to TPA alone at dose 50-100 µg/ml, and showed no differences compared to control at dose 100 µg/ml.

Figure 11:
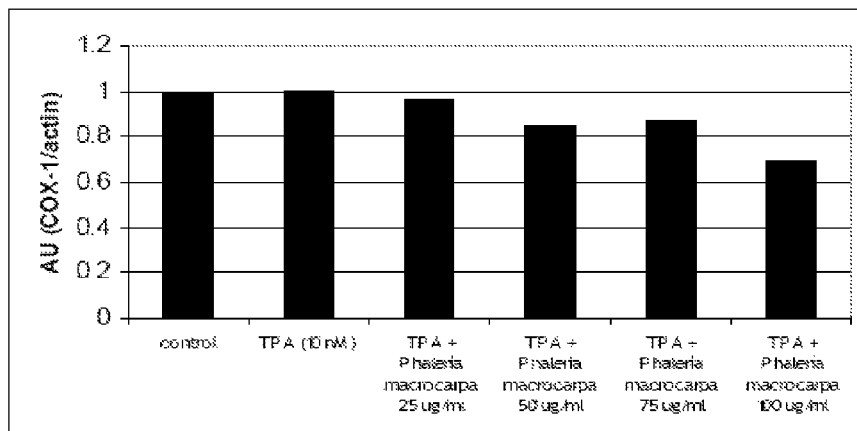
FIG. 11 shows COX-1 RT-PCR results; dosage variation of *Phaleria macrocarpa* extract (25-100 µg/ml) in MDA-MB-231 cells for 18 hours; the cells were previously serum-starved for 24 hours; induced with TPA 1 hour prior to *Phaleria macrocarpa* extract administration.

Administration of TPA alone and *Phaleria macrocarpa* extract 25 μg/ml an hour following TPA induction in MDA-MB-231 cells in serum-free condition did not show any significant differences on mRNA expression of COX-1 compared to control (FIG. 11). But at dose 50-100 μg/ml, COX-1 expression was relative slightly decreased compared to control and TPA alone.

Figure 12:
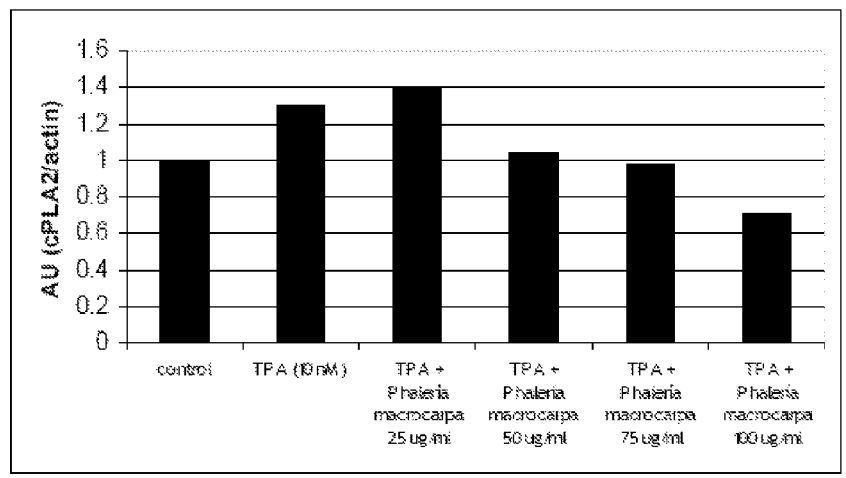
FIG. 12 shows $cPLA_2$ RT-PCR results; dosage variation of *Phaleria macrocarpa* extract (25-100 µg/ml) in MDA-MB-231 cells for 18 hours; the cells were previously serum-starved for 24 hours; induced with TPA 1 hour prior to *Phaleria macrocarpa* extract administration.

Administration of TPA showed an increase in $cPLA_2$ mRNA expression significantly compared to control in serum-free medium in MDA-MB-231 cells (FIG. 12). Administration of *Phaleria macrocarpa* extract 25 μg/ml following the TPA induction did not show any differences compared to TPA alone. Administration of the extract at dose 50-75 μg/ml following the TPA induction showed a down-regulation of $cPLA_2$ expression compared to TPA alone. Administration of *Phaleria macrocarpa* extract at dose 100 μg/ml following the TPA induction showed a significant decrease against control and TPA.

Figure 13:
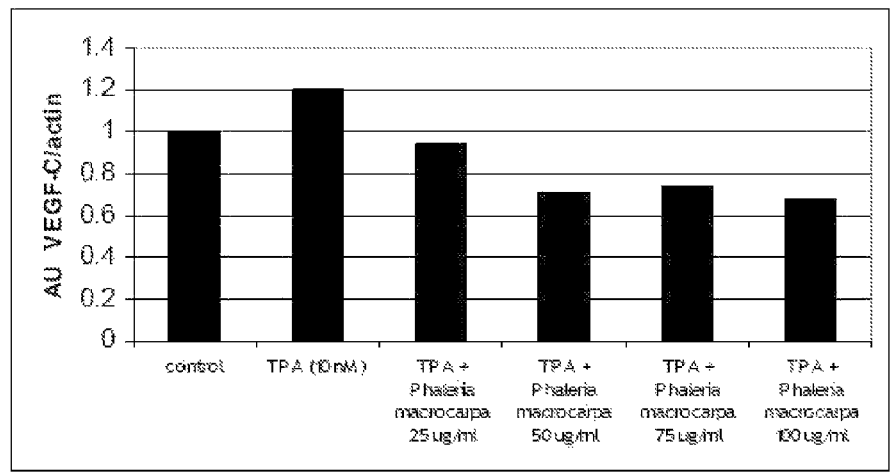
FIG. 13 shows VEGF-C RT-PCR results; dosage variation of *Phaleria macrocarpa* extract (25-100 µg/ml) in MDA-MB-231 cells for 18 hours; the cells were previously serum-starved for 24 hours; induced with TPA 1 hour prior to *Phaleria macrocarpa* extract administration.

Administration of TPA showed a significant increase of VEGF-C gene in mRNA level compared to control in serum-free medium in MDA-MB-231 cells (FIG. 13). Administration of *Phaleria macrocarpa* extract at dose 25 μg/ml following the TPA induction showed a decrease of VEGF-C compared to TPA alone. At dose 50-100 μg/ml following the TPA induction, it showed a significant decrease of VEGF-C mRNA expression compared to control and TPA alone.

Discussion

MDA-MB-231 is a breast cancer cell line which has doubling time of every 23 hours, thus its growth is relative fast enough to reach confluency. MDA-MB-231 cells can be injected to nude mice to promote breast tumor at such laboratory animals. MDA-MB-231 cells have no expression of E-cadherin, estrogen receptor, and progesterone receptor.

Some studies have shown that COX-2 is expressed abundantly in various kinds of cancerous tissue. In breast cancer, COX-2 gene expression is related to the growth of tumor, thus it has been a biological marker of breast cancer. Researchers have shown that high expression of COX-2 were present in highly invasive breast cancer cells with estrogen-independent characteristic (such as MDA-MB-231 cells), while less invasive breast cancer cells and estrogen-dependent characteristic (such as MCF-7 cells) did not express COX-2. Some steps of tumorigenesis metastasis such as cell proliferation, apoptosis, angiogenesis, cell motility enhancement, cell invasion, and immune system suppressive mediation, have been related to COX-2 expression. End products of COX-2 are prostaglandins and thromboxanes which mediate those steps in cancer cell progression.

Cyclooxygenase-2, abbreviated as COX-2, has been used as a target for prevention and treatment of many kinds of cancer. COX-1 and COX-2 are prostaglandin (PG) synthases which catalyze the synthesis of prostaglandin G2 (PGG2) and PGH2 from arachidonic acid (AA) by cyclooxygenase and peroxidase activities. Cyclooxygenase activity is inhibited by NSAIDs such as aspirin and sulindac, which commonly used to relieve pain and inflammation.

Effects of *Phaleria macrocarpa* extract (FIG. 10a) in serum-free condition have shown an inhibitory activity of COX-2 gene expression at the mRNA level. It showed that *Phaleria macrocarpa* extract has anti-inflammatory effect by inhibiting COX-2 gene expression. Administration of *Phaleria macrocarpa* extract an hour prior to tumor promoter TPA induction in MDA-MB-231 cells in serum-free condition showed an inhibitory of COX-2 expression in a dose-dependent manner (FIG. 10b). This showed that *Phaleria macrocarpa* extract can be used as preventive agent for breast cancer. Administration of *Phaleria macrocarpa* extract for an hour following tumor promoter TPA induction in MDA-MB-231 cells in serum-free condition also showed an inhibitory of COX-2 expression a dose-dependent manner (FIG. 10c). This showed that *Phaleria macrocarpa* extract can also be used as treatment or suppress the effect of tumor promoter in breast cancer cells. Besides, such inhibitory activity of COX-2 can be also used as treatment of rheumatoid arthritis, osteoarthritis, metabolic arthritis (acute gout), inflammatory arthropathies (ligament diseases) (such as: ankylosing spondylitis, psoriatic arthritis, Reiter's syndrome), dysmenorrhoea (menstrual pain), metastatic bone pain, headache and migraine, post-surgery pain, pain caused by inflammation and injury in tissues, pyrexia (fever), or renal colic (pain because of kidney stones).

COX-1 is expressed constitutively in body, administration of TPA did not show any significant differences compared to control. At dose 50-100 μg/ml, it showed an inhibition of COX-1, the inhibition is far less than the inhibition of the extract against COX-2. That showed that *Phaleria macrocarpa* was COX-2 selective inhibitor. Selective and nonselective COX-2 inhibition can inhibit tumor angiogenesis, decrease prostaglandin production by working on some potential cells such as tumor cells, endothelial cells, and stromal reactive cells.

COX-2 and $cPLA_2$ gene expressions can be induced by various hormones, cytokines, growth factors, or phorbol esters (such as TPA). The experiment results showed that there was an increase for both genes. $cPLA_2$ is activated because of the response to the agent that increase intracellular $Ca^{2+}$ which helps $cPLA_2$ translocation from cytosol into cell membrane, where the substrate is deposited: $cPLA_2$ helps to release AA from cell membrane to be used within cell. In PC3 cells, $PGE_2$ level increases as the increase of AA, the increase of $cPLA_2$ in mRNA level might be caused by the new $PGE_2$ synthesis than direct effect from AA. Activation of $cPLA_2$ expression might include the same mechanism with COX-2, because both genes have the same promoter elements.

Angiogenesis is important for tumor growth and development. The increase of tumor mass is caused by the increase of vascular supplies to deliver nutrient and oxygen into tumor. New blood vessel growth in tumor shows tumor metastasis development. Such process includes proliferation of endothelial cells which may be regulated by some growth factors. Among the polypeptides that are angiogenic, which stimulate endothelial cell proliferation in vitro and stimulate angiogenesis in vivo, VEGF is the factor secreted by tumor which was first discovered that can increase the vascular permeability also increase endothelial cell proliferation and migration. It has been known that COX-2 in mRNA level is highly correlated with VEGF-C mRNA level in breast cancer tissues in human and VEGF-C gene expression or secretion from breast cancer cell line. mRNA expression level of VEGF-C or COX-2 in breast cancer tissues is correlated with the expression of LYVE-1, which is a marker for lymphangiogenesis. When VEGF-C synthesis is stimulated in breast cancer cells, then so it does with COX-2 and the activity of EP1 and EP4 receptors. VEGF-C synthesis in MDA-MB-231 cells depends on Her-2/Neu, p38 MAPK and Src kinase. The experiment results showed an inhibitory of VEGF-C expression in mRNA level in MDA-MB-231 cells. This showed that *Phaleria macrocarpa* extract has antiangiogenic effect.

Conclusion

From the studies above, it is concluded that *Phaleria macrocarpa* extract is able to inhibit cyclooxygenase enzymes (cyclooxygenase inhibitor) that inhibits the expression of COX-2 and slightly COX-1 in mRNA level in breast cancer cells, MDA-MB-231, thus this extract has an anti-inflammatory activity. Beside that, it is also concluded that the extract inhibits the expression of $cPLA_2$ in mRNA level; it supports the extract activity as an anti-inflammation. The extract also inhibits the expression of VEGF-C in mRNA level, thus it has an antiangiogenic activity.

These conclusions also support the deduction that the extract can be used as anti-inflammatory, pain-reliever, or analgesic or painkiller, and/or body temperature lowering or fever-reliever, or antipyretic agent, also its combinations.

Beside that, the conclusions also show that the application of *Phaleria macrocarpa* extract in NSAIDs can be used to treat rheumatoid arthritis, osteoarthritis, metabolic arthritis (acute gout), inflammatory arthropathies (ligament diseases, such as: ankylosing spondylitis, psoriatic arthritis), Reiter's syndrome, dysmenorrhoea (menstrual pain), metastatic bone pain, headache and migraine, post-surgery pain, pain caused by inflammation and injury in tissues, pyrexia (fever), or renal colic (pain that commonly occurs because of kidney stones).

D. Pharmaceutical Dosage Forms

This invention also includes pharmaceutical compositions and dosage forms contained *Phaleria macrocarpa* extract in an amount that is effective as an active ingredient in a herb or mixed herbs dosage form, including carrying agents, excipients or additive substances that pharmaceutically acceptable and physiologically suitable.

In the process of making pharmaceutical composition according to this invention, active ingredient of *Phaleria macrocarpa* extract mixed with excipient(s), dissolved by excipient(s) or mixed in carrying agent(s) that can be made in form of capsule, sachet, paper, also other materials or other wrappers.

If pharmaceutically approved excipient is used as a solvent, the excipient can be in form of solid, semi-solid or liquid (oral and injection), that reacts as a carrier or medium for the active substance. Thus, pharmaceutical composition according to this invention can be made in form of pill, capsule, tablet, powder, sachet, solution, syrup, emulsion, suspension, effervescence tablets, gel, ointment, cream, and mouthwash, massage oil, suppository, or injection. Beside that, pharmaceutical composition contained *Phaleria macrocarpa* extract according to this invention can also be made as supplement, vitamin, also food and beverage production.

Some examples of suitable excipients are microcrystalline cellulose, gelatin, lactose, dextrose, sucrose, sorbitol, mannitol, flour, calcium phosphate, calcium silicate, etc. Formulation according to this invention may also contain lubricant agent (such as talc, stearic magnesium, and mineral oil), wetting agent, preservative agent, sweetener and flavoring.

Composition according to this invention can also be made with formulation that caused active ingredient to release directly, sustained, or controlled after the patient receives such dosage forms using methods that have been applied in pharmaceutical industry. Tablet or pill according to this invention can be layered to extend the half life of the extract thus its frequency of use can be reduced.

Method of formulating this extract in a solid form, such as tablet, can be done through the mix of the active ingredient, *Phaleria macrocarpa* extract, with excipient(s) to form an initial formulation contained homogeneous mix from the composition according to this invention. The initial formulation is a mix contained the active ingredient of the *Phaleria macrocarpa* extract dispersed homogeneously so it can be properly distributed into the required dose in a dosage form, for example capsule, tablet, or pill.

Tablet or pill according to this invention can be added with a protection layer to reduce or cover bitter from the composition or active substance of *Phaleria macrocarpa* extract.

*Phaleria macrocarpa* extract in effective amount or dose according to this invention is the amount or dose which the *Phaleria macrocarpa* extract able to inhibit the growth of breast cancer cells and/or other gynecologic pathologic cells. The effective amount depends on the physical condition of the patient, including weight, age, etc, and also depends on the type, size, and amount of cancer cells and other targeted pathologies. According to this invention, preferably the amount of *Phaleria macrocarpa* extract in a single or mixed formulation is in a range of 25-2000 mg per day.

This present invention also anticipates the therapeutic use of *Phaleria macrocarpa* extract as prevention, concurrent, or after intrusive surgery to carry or take out neoplasm mass. The *Phaleria macrocarpa* extract can be given directly to or around the location of neoplasm mass carried out from such intrusive surgery.

This present invention also anticipates the therapeutic use of *Phaleria macrocarpa* extract that is used with or after the radiotherapy.

This present invention also anticipates the use of *Phaleria macrocarpa* extract together with or additional to the composition of anticancer or other chemotherapeutic substances available in market, also other drugs that are used for gynecologic medications.

E. Industrial Application

Extract or pharmaceutical dosage forms of this *Phaleria macrocarpa* extract can be used in industrial scale in production of extract, powder extract, and/or pharmaceutical dosage forms mainly for oral dosage form such as solid, semi-solid, or liquid that is used as antineoplastic, anti-inflammatory, and antiangiogenic agent against cancer cells and other gynecologic pathologic cells.

The invention claimed is:

1. A method comprising: administering to a patient in need of treatment for inflammation at effective amount of an extract of *Phaleria macrocarpa* fruit, obtained by
   a) grinding the flesh of *phaleria macrocarpa* fruit to obtain a dry powder,
   b) extracting the dry powder obtained in a) using an organic solvent,
   c) evaporating the organic solvent obtained in b) to a dried extract,
   d) fractionating the dried extract obtained in c) by liquid-liquid extraction, using an organic solvent and water,
   e) isolating and drying the organic phase obtained in d), and
   f) evaporating the dried organic solvent in e).

2. The method of claim 1 wherein said medicament reduces the level of arachidonic acid within cells.

3. The method of claim 1, wherein said medicament inhibits cyclooxygenase.

4. The method of claim 1, wherein said medicament reduces prostaglandin levels.

5. The method of claim 1, wherein said medicament relieves pain.

6. The method of claim 1, wherein said medicament is administered in a dietary supplement.

7. The method of claim 6, wherein the dietary supplement is a tablet, capsule, syrup, effervescent, gel, ointment, cream, mouthwash, food or beverage product.

8. A method comprising: administering to a patient in need of treatment for angiogenesis, an effective amount of an extract of *Phaleria macrocarpa* fruit, obtained by a) grinding the flesh of *Phaleria macrocarpa* fruit to obtain a dry powder,
b) extracting the dry powder obtained in a) using an organic solvent,
c) evaporating the organic solvent obtained in b) to a dried extract.
d) fractionating the dried extract obtained in c) by liquid-liquid extraction, using an organic solvent and water,
e) isolating and drying the organic phase obtained in d), and
f) evaporating the dried organic solvent in e).

9. The method of claim 8, wherein said medicament reduces VEGF-C level.

10. The method of claim 8, wherein said medicament inhibits formation of new blood vessels.

11. The method of claim 8, wherein said medicament is administered in a dietary supplement

12. The method of claim 11, wherein the dietary supplement is a tablet, capsule, syrup, effervescent, gel, ointment, cream, mouthwash, food or beverage product.

* * * * *